United States Patent [19]

Garcia

[11] 4,400,158
[45] Aug. 23, 1983

[54] CONTROL RELEASE FOR A TOOL GRIP FOR A DENTAL HANDPIECE

[75] Inventor: Philippe Garcia, Besancon, France

[73] Assignee: Micro Mega Societe Anonyme, France

[21] Appl. No.: 286,071

[22] Filed: Jul. 23, 1981

[30] Foreign Application Priority Data

Sep. 5, 1980 [FR] France ............................ 80 19598

[51] Int. Cl.³ .......................... A61C 1/08; A61C 1/14
[52] U.S. Cl. ................................... 433/127; 433/129
[58] Field of Search ...................... 433/129, 126, 127; 279/51, 50, 57, 58, 74, 75, 122

[56] References Cited

U.S. PATENT DOCUMENTS

| 232,311 | 9/1880 | Starr | 433/129 |
|---|---|---|---|
| 239,597 | 4/1881 | Bergen | 279/51 |
| 548,988 | 10/1895 | Hood et al. | 433/129 |
| 1,349,832 | 8/1920 | Graves | 433/129 |
| 3,217,519 | 11/1965 | Demler | 279/57 |
| 3,475,817 | 11/1969 | Loge | 433/129 |

FOREIGN PATENT DOCUMENTS

| 644094 | 4/1937 | Fed. Rep. of Germany | 433/129 |
|---|---|---|---|
| 471112 | 5/1952 | Italy | 433/129 |
| 471284 | 5/1952 | Italy | 433/129 |
| 553835 | 1/1957 | Italy | 433/129 |

*Primary Examiner*—Gene Mancene
*Assistant Examiner*—John J. Wilson
*Attorney, Agent, or Firm*—Mason, Fenwick & Lawrence

[57] ABSTRACT

A dental handpiece has a hollow main body enclosing a central rotating spindle equipped with tool grip means adjacent its forward end; spring means effects axial movement of the spindle in an inward direction for actuating the tool grip means to provide a gripping function and release means moves the spindle outwardly against the bias of the spring means for deactivating the tool grip means with the release means including a unitary plate removably mounted in the main body with first and second levers being pivotally mounted on opposite sides of the plate so as to be substantially positioned within the confines of the main body; driving ends of the levers are engageable with the spindle for moving the spindle axially outwardly of the main body to deactivate the grip means. The levers are on diametrically opposite sides of the axis of the handpiece and are mounted for pivotal movement in a plane passing through the axis of the hand instrument.

8 Claims, 8 Drawing Figures

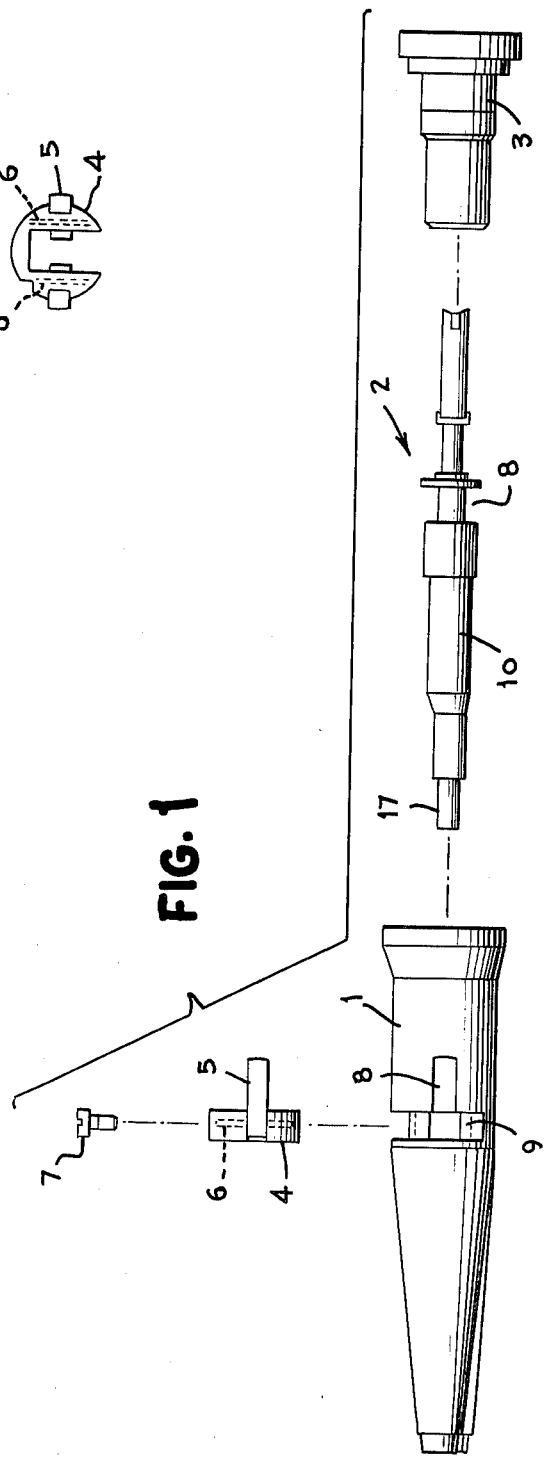
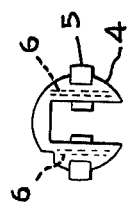
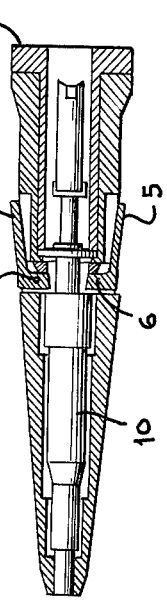
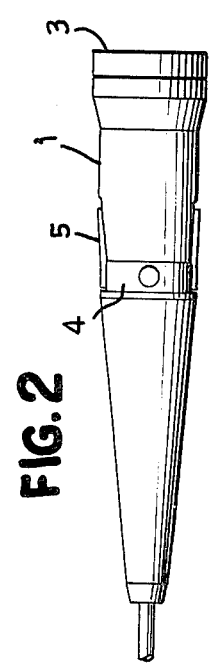
FIG. 1A
FIG. 1
FIG. 2
FIG. 3

CONTROL RELEASE FOR A TOOL GRIP FOR A DENTAL HANDPIECE

DESCRIPTIVE SUMMARY

The object of the invention is a control device for a clamping grip for a manual instrument.

According to the invention, two levers (5) hinged on a plate (4) fixed on the body (1) of the hand instrument axially displace the sliding device (10) which operates in conjunction with the spring of the clamping grip.

Application

Dentistry hand instruments with internal spray tubes. Figure of the summary, FIG. 1.

The object of the present invention is a hand instrument for a micromotor consisting of a main body in which the central rotating spindle equipped in its front part with the clamping grip of the tool, is supported, between bearings, the respective closing and opening of the said clamping grip being controlled by a clamping mechanism which consists of a spring supported on the one hand on a fixed stop and on the other hand on an axially movable element which can be actuated from outside by manual action on the part of the operator.

A device of this type has already been described in the French Pat. No. 75/39915 and in its Addition Certificate No. 76/32151 in the name of the applicant.

In the known devices, the axially movable element which causes the compression or release of the spring is integral with a clamping bearing which slides longitudinally in the main patent, or can be rotated in the addition certificate. The movement of these clamping bearings results, by means of the cooperation of ramps with balls which are regularly distributed over the periphery of the instrument, in the transmission of pressure from the rear to the front on the clamping grip.

Although nowadays these devices still give complete satisfaction for the majority of usual dental applications, nevertheless there is an obstacle in that it is almost impossible to pass spray tubes through the body of the hand instrument, for the supply to the tool which is carried by the hand instrument. This is in fact made impossible owing to the very structure of the device with balls and external bearing.

The object of the present invention is to mitigate this drawback of the devices know to previous technology.

In accordance with the invention, the hand instrument for a micromotor, as described above, is characterized by the fact that the axial displacement of the moving element acting on the spring of the clamping mechanism of the grip is ensured by a device which consists of at least one lever which can be actuated by the operator.

In a very advantageous manner, the control device will consist of two levers which are hinged on a plate the two levers being diametrically opposite in relation to the axis of the hand instrument and being able to pivot in a plane which passes through the axis of the hand instrument.

Hence a device of simple, economical design is obtained, which makes it possible to control the clamping device of the grip by simple manual pressure on the levers. Basically this device especially permits the positioning of the desired spray tubes inside the body of the hand instrument with a hand instrument body made in one piece.

In an advantageous manner the plate supporting the two levers will be fixed on the body of the hand instrument by a simple clamping screw. Hence, it is very easy to withdraw the plate and lever unit in order to carry out various cleaning and maintenance operations on the internal components of the hand instrument.

The invention will be better understood by means of the description given below with reference to the attached drawings in which:

FIG. 1 is an exploded diagram of the various component parts of a hand instrument according to the invention;

FIG. 1A is an end elevation of the plate;

FIG. 2 is a view of the hand instrument of FIG. 1 from above in the utilisation position;

FIG. 3 is a longitudinal cross section view of the instrument shown in FIG. 2;

Figure 4:
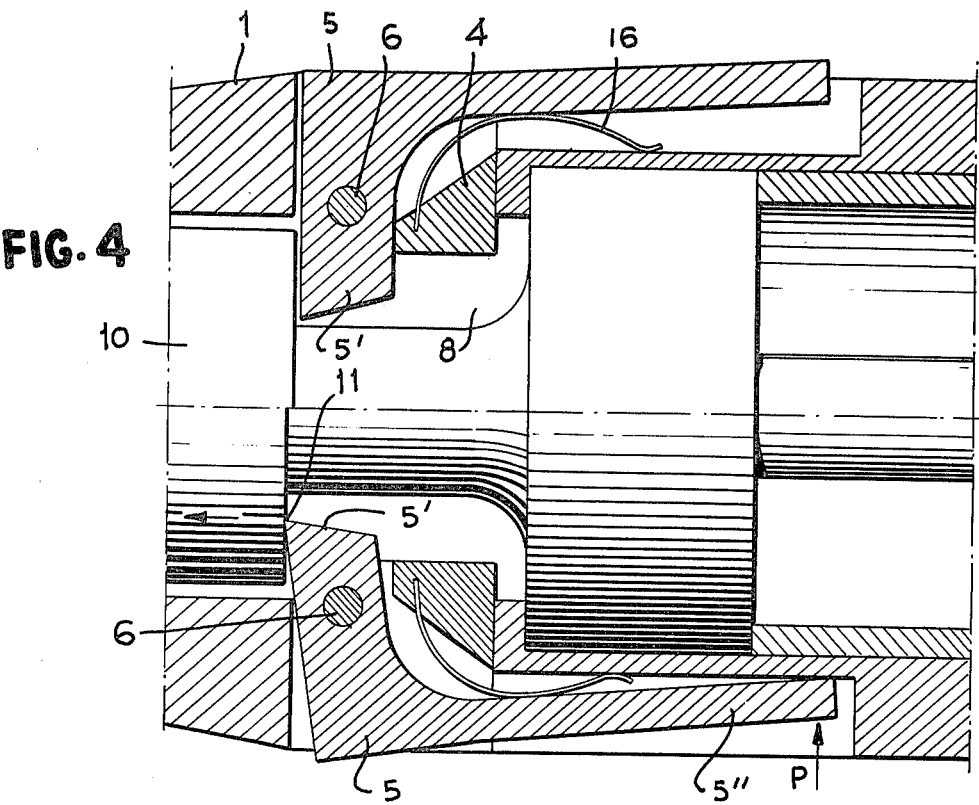
FIG. 4 is an enlarged partial longitudinal cross section view according to FIG. 3 at the level of the levers, one of the levers being in the closed position and the other in the open position of the grip.

The dentistry hand instrument consists, in a manner which is known in itself, of a body (1), a clamping mechanism (2) consisting of a spindle, a bearing and a driving device. The clamping mechanism will now be described in detail, reference being made here to the already mentioned French Pat. Nos. 75/39915 and 76/32151.

At the end of the body (1) a bearing (3) is screwed in which immobilises the whole of the clamping mechanism in a translation movement whilst, however, permitting it to rotate freely.

According to the invention, there is positioned on the body (1) of the hand instrument, in a corresponding recess (9) provided for this purpose, a plate (4) equipped with two levers (5) which are diametrically opposite in relation to the axis of the hand instrument and which can each pivot in a plane which passes through the axis of the hand instrument, around a spindle (6) fixed to the plate (4). The arms of the levers (5) come into position in the symmetrical seatings (8) arranged on the housing (1) parallel to the axis of the hand instrument and emerging on to the recess (9).

The clamping mechanism which consists of a shaft (17) and a sliding device (10) consisting of a spring which compresses the clamping grip, makes it possible by means of deformation, to clamp a tool such as, for example, a drill.

In order to insert the tool, the sliding device (10) is displaced axially by actuating the two levers (5). FIG. 4 should now be referred to for the kinematics of the mechanism. On the upper part of the drawing the lever is shown in the closed position of the instrument. The arm (5') of the lever (5) is hence not in contact with the front face of the sliding device (10). By exerting on the branch (5'') of the lever (5) a manual pressure shown diagrammatically by the arrow P, the pivoting of the lever around its axis (6) is brought about and hence a contact (11) between the end of the arm (5') of the lever (5) and the front face of the sliding device (10). The device (10) then slides, which has the effect of freeing the grip from the action of the spring and making it possible to remove or insert the tool.

If the manual pressure exerted on the arm (5") of the lever is released, a return spring (16) returns the levers back to the rest position. This is important because it must be kept in view that the whole of the clamping device and hence the instrument (10) rotates during the operation of the manual instrument.

Figure 5:
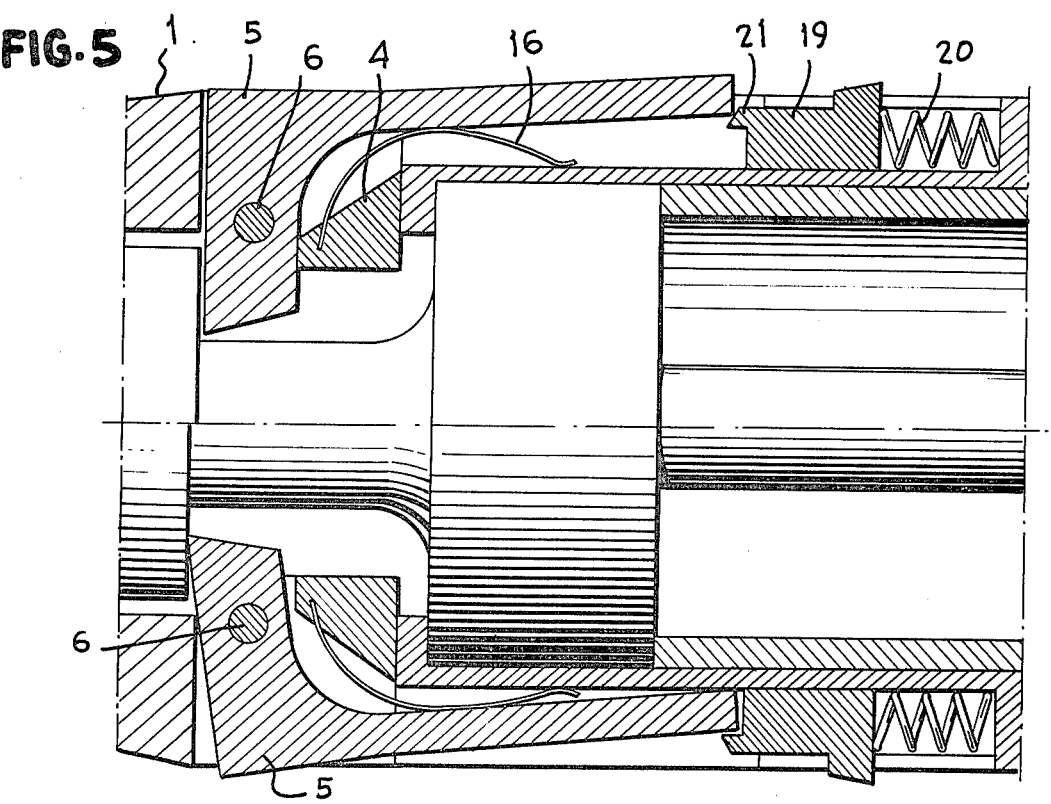
FIG. 5 is a variant of the execution of the lever device of FIG. 4.

In the variant of FIG. 5, the levers are held in their position for unlocking the grip by retractable slides (19) returned by a spring (20), the said slides consisting of a stop (21) which holds the arm (5") of the lever automatically when the latter has been actuated. To release the lever the slides (19) are displaced towards the back of the hand instrument, the levers resume their rest position under the action of the return springs (16). This makes it possible to change the two without having to actuate the mechanism twice, once for removing a tool, the other for inserting the new tool.

Figure 6:
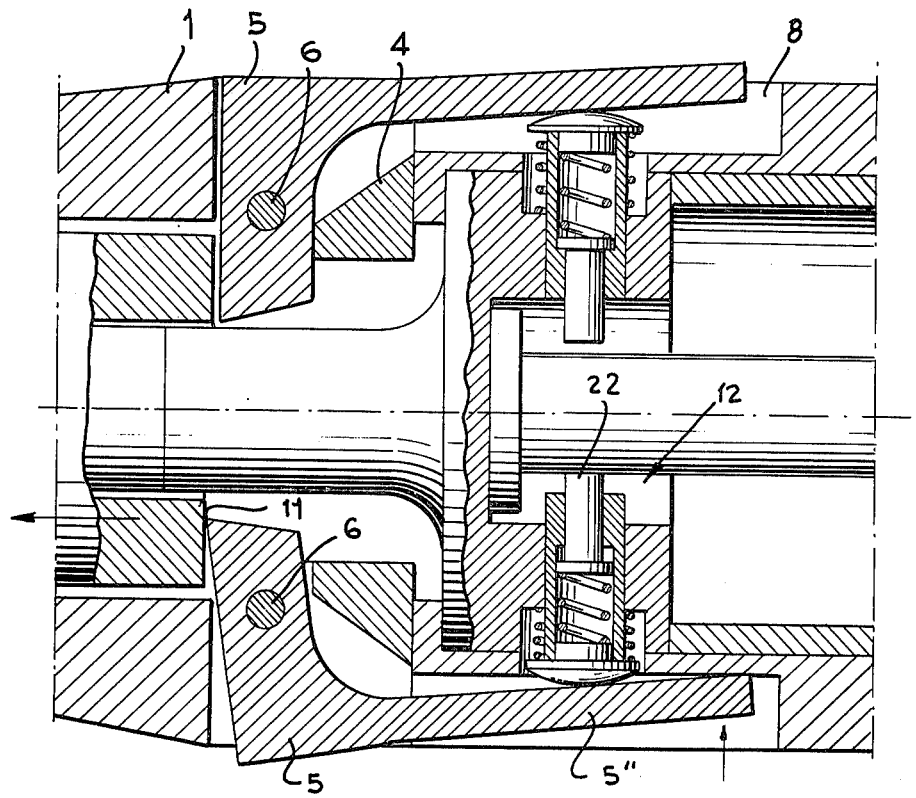
FIG. 6 is another variant of the execution of the lever device of FIG. 4.

In the version of FIG. 6, the actuation of the levers (5) also makes it possible in addition to unlocking the clamping grip, to ensure, by means of a push button device (12) that the shaft (17) is immobilised.

In the first part of the rocking movement of the lever (5), before contact (11) with the front face of the sliding device (10) takes place, the arm (5") of the lever is supported on the push button (12) which is returned by a spring, and this immobilises the shaft (17) by means of a shoe (22). This prevents the user of the hand instrument from beginning to actuate the clamping device before the shaft (17) is totally immobilised, the system having a certain inertia. Hence it is possible to avoid the deterioration of the grip and also of the levers which would be applied to a clamping device which was still rotating.

Figure 7:
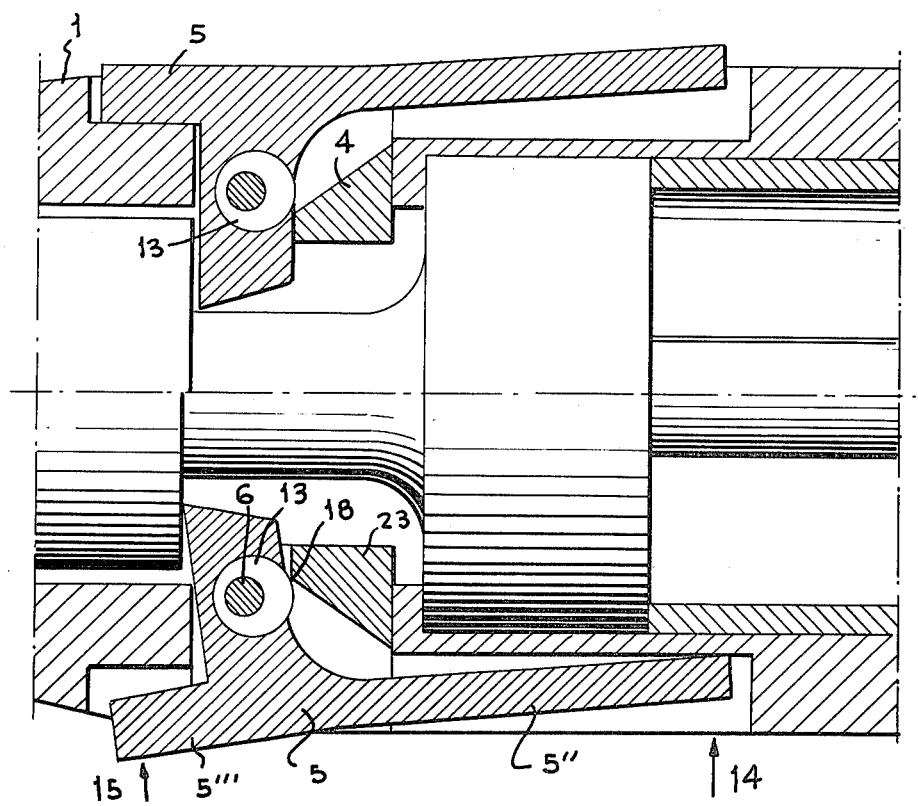
FIG. 7 is another variant of the execution of the lever device of FIG. 4.

In the embodiment of FIG. 7 finally, the two levers (5) are each equipped with a cam (13) which is integral with the latter, making a wedging possible at the point of contact (18) of the plate (4) with the body (23) in the unlocking position of the clamping grip. This position is achieved by pressure at (14) on the arm (5"). For the unlocking of the lever and in the locking of the tool the pressure is exerted on an arm (5") at (15), the arm (5") being opposite to the arm (5") in relation to the pivoting axis (6). In this case it is not necessary to provide a return spring.

The combination of the achievements described offers the following fundamental advantages:
possibility of obtaining a hand instrument with internal passage of spray;
a hand instrument body which is all in one price;
plate and levers made from a unit which can easily be removed from the hand instrument by unlocking of the screw (7) shown in FIG. 1.

I claim:

1. In a dental handpiece including a main body, a central rotating spindle equipped with tool grip means adjacent a forward end portion and spring means for effecting axial movement of the spindle in an inward direction for actuating said tool grip means to provide a gripping function; the improvement comprising improved release means for moving the spindle outwardly against the bias of said spring means for deactivating said tool grip means wherein said release improved means comprises a unitary plate removably mounted in the main body, first and second levers pivotally mounted on opposite sides of the plate so as to be substantially positioned within the confines of said main body and having driving ends engageable with said spindle for moving the spindle axially outwardly of the main body in response to pivotal movement of said levers inwardly of said body by a user for effecting deactivation of said tool grip means, said first and second levers being on diametrically opposite sides of the axis of the hand instrument and being mounted for pivotal movement in a plane passing through the axis of the hand instrument.

2. A dental handpiece according to claim 1 wherein said main body includes a transverse recess in which said plate is removably positioned and also includes axially parallel grooves communicating with said recess in which the manually engageable portion of said levers are positioned.

3. A dental handpiece according to claim 2 additionally including spring means for urging said levers outwardly in a direction to disengage their driving ends from driving contact with said spindle.

4. A dental handpiece according to claim 3 additionally including slide latch means mounted on said main body for holding said levers in their inward position when in a latching position and spring means for urging said slide latch toward said latching position.

5. A dental handpiece according to claim 2 additionally including push buttons respectively engaged with each of said levers on one end and having a braking shoe on an opposite end which is moved into contact with the spindle in response to movement of the associated lever to its inward position for stopping rotation of the spindle in conjunction with deactivation of said tool grip means.

6. A dental handpiece according to claim 1 wherein said unitary plate is of U-shaped configuration including side legs having a central opening therebetween and wherein said central opening is fitted over and straddles said spindle and said levers are each respectively mounted on a different one of said side legs.

7. A dental handpiece according to claim 6 wherein said main body includes a transverse recess in which said plate is removably positioned and also includes axially parallel grooves communicating with said recess in which the manually engageable portion of said levers are positioned.

8. A dental handpiece according to claim 7 additionally including spring means for urging said levers outwardly in a direction to disengage their driving ends from driving contact with said spindle.

* * * * *